United States Patent [19]

Kampfer et al.

[11] Patent Number: 4,483,799

[45] Date of Patent: Nov. 20, 1984

[54] HYDROXY ALKANE SULFONIC ACID SULFOALKYL ESTERS

[75] Inventors: Helmut Kampfer, Cologne; Detlef Wendisch; Marie Hase, both of Bergisch Gladbach, all of Fed. Rep. of Germany

[73] Assignee: Agfa-Gevaert Aktiengesellschaft, Leverkusen, Fed. Rep. of Germany

[21] Appl. No.: 230,321

[22] Filed: Feb. 2, 1981

[30] Foreign Application Priority Data

Feb. 8, 1980 [DE]  Fed. Rep. of Germany ....... 3004692

[51] Int. Cl.$^3$ ............................................ C07C 143/68
[52] U.S. Cl. ............................ 260/456 R; 260/513 N
[58] Field of Search .................................... 260/456 R

[56] References Cited

PUBLICATIONS

Manecke, Chem. Ber., 85, 160 (1952).

*Primary Examiner*—Nicky Chan
*Attorney, Agent, or Firm*—Connolly and Hutz

[57] ABSTRACT

Sulfoalkylating agents free from sultones may be obtained by heating hydroxy alkane sulfonic acids of propane or butane or the corresponding sultones having 5 or 6 ring members with up to four times the molar quantity of water to a temperature in the region of from 80° to 180° C. The sulfoalkylating agents are believed to be the "dimeric esters" of the hydroxy alkane sulfonic acids.

2 Claims, No Drawings

HYDROXY ALKANE SULFONIC ACID SULFOALKYL ESTERS

This invention relates to hydroxy alkane sulfonic acid sulfoalkyl esters and to a process for their preparation.

Sulfonic acid esters are generally prepared from sulfonic acid halides and the appropriate alcohols. They are excellent alkylating agents. A special group of sulfonic acid esters is derived from hydroxy alkane sulfonic acids by intramolecular ester formation. Among the cyclic internal esters known as sulfonylides, the sultones have achieved a position of considerable commercial importance as sulfoalkylating agents. The 5-membered 1,3-propane sultones (=1,2-oxathiolane-2,2-dioxides) are particularly important sultones because of their high reactivity towards compounds which are capable of being alkylated. They can easily be obtained from 3-hydroxy- or 3-halogenpropane sulfonic acids by a cyclization reaction carried out at elevated temperature and accompanied by distillation under vacuum. One disadvantage of sultones is their physiological effect and the attendent problems of storage, transport and handling in general. There have therefore been many attempts to replace sultones by other, physiologically harmless, sulfoalkylating agents.

Hydroxy alkane sulfonic acids and their salts, for example, have been described as quaternizing agents for hetero cyclic tertiary amines. O-Sulphoalkylimido esters and uronium salts have been recommended for the same purpose. These methods are, however, restricted to tertiary bases and are less generally applicable than sultones. Furthermore, imido esters and uronium salts are relatively expensive to manufacture.

For these reasons there has been considerable interest in finding inexpensive, physiologically harmless substitutes for sultones which will be free from the disadvantages mentioned above.

The present invention relates to sulfoalkylating agents presumably of a structure of the following formula I intermolecular dimeric "esters" of hydroxy alkane sulfonic acid or "dimeric hydroxyalkane sulfonic acid":

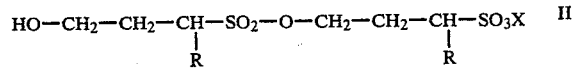

in which
R represents hydrogen or alkyl with 1 to 4 carbon atoms, in particular methyl, which alkyl group may be substituted, for example by halogen such as fluorine or chlorine;
X represents hydrogen or a cation, preferably an alkali metal cation or ammonium ion, and
n=3 or 4, preferably 3.

Compounds corresponding to the following formula II:

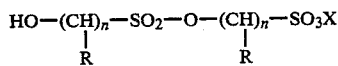

in which R and X have the meaning indicated above are particularly suitable.

The invention also relates to a process for the preparation of the "esters" of formula I by heating the corresponding hydroxy alkane sulfonic acids, preferably those of formula III, or the corresponding alkane sultones preferably those of formula IV, in which R has the meaning indicated above, to temperatures in the region of from 80° to 180° C., preferably from 120° to 150° C., in the presence of water in an amount of 1 to 4 moles per mole of the hydroxy alkane sulfonic acid or sultone.

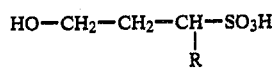

The sulfoalkylating agents of the invention which may be obtained by the process described herein before are hygroscopic substances which crystallize with 1 to 1.5 mol of water. They hydrolyse in dilute aqueous solution to form the hydroxy alkane sulfonic acids. When heated under dehydrating conditions such as removal of water by evaporation, azeotropic distillation or the presence of water binding agents, they cyclize readily to the corresponding sultone. The $^{13}C$ shifts of the NMR spectra of the sulfoalkylating agents are in agreement with the ester structure of formula I above.

The sulfoalkylating agents of the invention may be used instead of the usual sultones, e.g. instead of 1,3-propane sultones, for the sulfoalkylating of suitable compounds which have functional groups containing O, S, N or P. Because of the simple method by which they can be prepared and the ease with which they can be recycled to sultones, the "esters" may be used as an environmentally harmless "form of transport for sultones".

Recyclization followed by sulfoalkylating may be carried out in a single operation in sealed reaction vessels, so that the release of harmful sultones is avoided. The preparation of 3-hydroxy alkane sulfonic acids suitable as starting materials for the "esters" I has been described in German Offenlegungsschrift No. 2,803,493 and the preparation of the corresponding sultones in the monograph by D. S. Breslow and H. Skolnik entitled "Multi-Sulfur and Sulfur and Oxygen Five- and Six-membered Heterocycles", Chapter 4, page 78 et seq Interscience Publishers 1966.

The "esters" according to the invention may be used, for example, for the sulfoalkylation of amines which may be alkylated or arylated to produce valuable intermediate products for textile auxiliaries. The esters may also be used for the preparation of wetting agents, e.g. by reaction with long chain alcohols. Hydrophilic properties may be imparted to high molecular weight substances such as cellulose or proteins by treating them with the "esters".

The preparation of some alkylating agents according to the invention is described below. Other compounds corresponding to formula I are prepared in a similar manner.

EXAMPLE 1

3-Hydroxy propane sulfonic acid-(3-sulfopropyl)-ester ("ester 1")

(a) 1 mol of 1,3-propane sultone is heated under reflux with 3 mol of water at 137° C. for 2 hours. The reaction product is then freed from excess water on a rotary evaporator under a vacuum of 0.3 mm at 40° C. The ester is obtained as a viscous oil which crystallizes when left to stand and still contains 9% of water after titration. According to the $^{13}$C NMR spectrum, this product is free from 1,3-propane sultone.

(b) 1 mol of 3-hydroxy propane sulfonic acid is heated to 137° C. with 3 mol of water for 2 hours. Further treatment as described under (a) results in a crystallizing oil which has a water content of 8% and is also free from 1,3-propane sultone.

Recyclization:

1,3-propane sultone is recovered in 88% yield by 4 hours heating of "ester 1" to 140° C. (bath temperature) under a vacuum of 20 mm while the water formed in the reaction is distilled off.

EXAMPLE 2

4-hydroxy butane-2-sulfonic acid-(3-sulfobutyl)-ester ("ester 2")

4-hydroxy butane-2-sulfonic acid having a water content of 14.7% is heated on an oil bath temperature of 170° C. for 2 hours, with the reaction mixture at a temperature of 144°–146° C. The water split off in the reaction is then evaporated off under a vacuum of 0.5 mm and a temperature of 40° C., using a receiver cooled to −38° C. The yield determined by the $^{13}$C NMR spectrum is 96.6%.

The alkylating agents according to the invention as prepared and described in Examples 1 and 2 are characterized by the NMR spectroscopic data, by comparison with the corresponding hydroxy alkane sulfonic acids (5) and (6) and 1,3-propane sultones (3) and (4). The tables indicate the $^{13}$C-shifts (ppm, relative to TMS=0, determined in D$_2$O with dioxane as internal reference; δ=67,4 ppm, relative to TMS=0).

Table 1 shows the $^{13}$C-shifts of 3-hydroxy propane sulfonic acid (3-sulfopropyl)-ester (1) determined in D$_2$O.

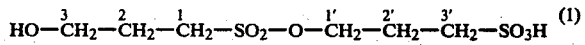

HO—$\overset{3}{\text{CH}_2}$—$\overset{2}{\text{CH}_2}$—$\overset{1}{\text{CH}_2}$—SO$_2$—O—$\overset{1'}{\text{CH}_2}$—$\overset{2'}{\text{CH}_2}$—$\overset{3'}{\text{CH}_2}$—SO$_3$H  (1)

TABLE 1

| $^{13}$C shifts (ppm, relative to TMS = 0) of (1) in D$_2$O. | |
|---|---|
| C-Atom | δ (ppm) |
| 1 | 48.8 |
| 2 | 27.8 |
| 3 | 61.1 |
| 1' | 69.5 |
| 2' | 25.2 |
| 3' | 48.8 |

Table 2 contains the $^{13}$C shifts of 4-hydroxy butane-2-sulfonic acid-(3-sulfobutyl)-ester (2) in D$_2$O.

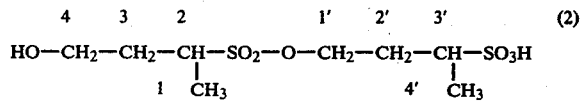

HO—CH$_2$—CH$_2$—$\overset{2}{\text{CH}}$—SO$_2$—O—CH$_2$—CH$_2$—$\overset{2'}{\text{CH}}$—SO$_3$H  (2)
           |                                    |
       1  CH$_3$                            4' CH$_3$ (positions: 4 3 2  1' 2' 3')

TABLE 2

| $^{13}$C shifts (ppm, relative to TMS = 0) of (2) in D$_2$O. | |
|---|---|
| C-Atom | δ (ppm) |
| 1 | 15.4 |
| 2 | 53.6* |

TABLE 2-continued

| $^{13}$C shifts (ppm, relative to TMS = 0) of (2) in D$_2$O. | |
|---|---|
| C-Atom | δ (ppm) |
| 3 | 34.4 |
| 4 | 60.0 |
| 1' | 68.5 |
| 2' | 31.7 |
| 3' | 53.5* |
| 4' | 15.4 |

The signals marked by an asterisk (*) may coalesce to one signal due to experimental conditions.

The $^{13}$C data of (1) and (2) differ distinctly from those of (3) and (4).

Table 3 shows the $^{13}$C shifts of 1,3-propane sultone (3) while Table 4 contains those of 3-methyl-1,3-propane sultone (4).

Tables 5 and 6 give the $^{13}$C data of 4-hydroxy propane sulfonic acid (5) and of 4-hydroxy butane-2-sulfonic acid (6).

TABLE 3

| $^{13}$C shifts (ppm, relative to TMS = 0) of (3) in D$_2$O. | |
|---|---|
| C-Atom | δ (ppm) |
| 1 | 72.3 |
| 2 | 24.4 |
| 3 | 45.3 |

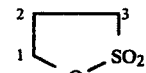

(3)

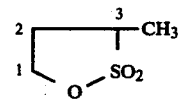

(4)

TABLE 4

| $^{13}$C shifts (ppm, relative to TMS = 0) of (4) in D$_2$O. | |
|---|---|
| C-Atom | δ (ppm) |
| 1 | 70.3 |
| 2 | 31.4 |
| 3 | 52.3 |
| CH$_3$ on 3 | 13.3 |

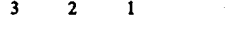

HO—CH$_2$—CH$_2$—CH$_2$—SO$_3$H   (5)

(positions: 3 2 1)

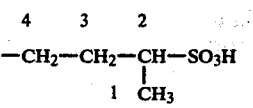

HO—CH$_2$—CH$_2$—CH—SO$_3$H   (6)
                   |
               1  CH$_3$ (positions: 4 3 2)

TABLE 5

| $^{13}$C shifts (ppm, relative to TMS = 0) of (5) in D$_2$O. | |
|---|---|
| C-Atom | δ (ppm) |
| 1 | 48.9 |
| 2 | 27.8 |
| 3 | 61.2 |

TABLE 6

| $^{13}$C shifts (ppm, relative to TMS = 0) of (6) in $D_2O$. | |
| --- | --- |
| C-Atom | δ (ppm) |
| 1 | 15.4 |
| 2 | 53.4 |
| 3 | 34.4 |
| 4 | 60.0 |

All the measurements were carried out at 25.2 MHz using an XL-100-15″ Spectrometer of VARIAN ASSOCIATES, Palo Alto, Calif./U.S.A., operating with PFT under proton noise decoupling. $D_2O$ was used as solvent and deuterium lock. Dioxane was used as internal reference (δ=67.4 ppm, relative to TMS=0). The accuracy of shift measurement is ±0.1 ppm.

We claim:

1. Sulfoalkylating agent, obtainable by heating 3-hydroxypropane sulfonic acid or 1,3-propane sultone to a temperature in the region of from 80° to 180° C. in the presence of water in an amount of from 1 to 4 moles per mole of 3-hydroxy propane sulfonic acid or 1,3-propane sultone, and characterized by the following $^{13}$C-NMR-shifts (ppm, relative to TMS=0, in $D_2O$ in the presence of dioxane): 25.2; 27.8; 48,8; 61.1 and 69.5.

2. Sulfoalkylating agent, obtainable by heating 4-hydroxy butane-2-sulfonic acid or 3-methyl-1,3-propane sultone to a temperature in the region of from 80° to 180° C. in the presence of water in an amount of from 1 to 4 moles per mol of 4-hydroxy-butane-2-sulfonic acid or 3-methyl-1,3-propane sultone, and characterized by the following $^{13}$C-NMR-shifts (ppm, relative to TMS=0, in the presence of dioxane): 15.4; 31.7; 34.4; 53.6; 60.0 and 68.5.

* * * * *